(12) United States Patent
Towe et al.

(10) Patent No.: US 11,400,318 B2
(45) Date of Patent: *Aug. 2, 2022

(54) APPARATUS, SYSTEM, AND METHOD FOR NEUROSTIMULATION BY HIGH FREQUENCY ULTRASOUND

(71) Applicant: ARIZONA BOARD OF REGENTS ON BEHALF OF ARIZONA STATE UNIVERSITY, Scottsdale, AZ (US)

(72) Inventors: Bruce C. Towe, Mesa, AZ (US); Daniel Gulick, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 558 days.

This patent is subject to a terminal disclaimer.

(21) Appl. No.: 16/363,304

(22) Filed: Mar. 25, 2019

(65) Prior Publication Data

US 2019/0282835 A1    Sep. 19, 2019

Related U.S. Application Data

(63) Continuation of application No. 14/402,632, filed as application No. PCT/US2013/030812 on Mar. 13, 2013, now Pat. No. 10,252,085.

(Continued)

(51) Int. Cl.
*A61N 7/00* (2006.01)
*A61N 1/05* (2006.01)
*A61N 1/36* (2006.01)

(52) U.S. Cl.
CPC ............. *A61N 7/00* (2013.01); *A61N 1/0504* (2013.01); *A61N 1/3605* (2013.01); *A61N 2007/0026* (2013.01); *A61N 2007/0034* (2013.01)

(58) Field of Classification Search
CPC ...... A61N 7/00; A61N 1/0504; A61N 1/3605; A61N 2007/0034; A61N 2007/0026; A61N 1/37217; A61N 1/3787
See application file for complete search history.

(56) References Cited

U.S. PATENT DOCUMENTS

| 4,935,345 A | 6/1990 | Guilbeau et al. |
| 5,070,873 A | 12/1991 | Graupe et al. |

(Continued)

FOREIGN PATENT DOCUMENTS

| WO | 2004016315 A1 | 2/2004 |
| WO | 2004105583 A2 | 12/2004 |

(Continued)

OTHER PUBLICATIONS

PCT/US2013/030812 International Search Report and Written Opinion dated Jun. 26, 2013.
U.S. Appl. No. 16/515,460.

*Primary Examiner* — Hien N Nguyen
(74) *Attorney, Agent, or Firm* — Lewis Roca Rothgerber Christie LLP

(57) ABSTRACT

An apparatus, system, and method for neurostimulation by high frequency ultrasound. In one embodiment, an apparatus includes a pulse generator, an ultrasound transducer coupled to the pulse generator, and an implantable stimulator. The implantable stimulator may include a piezoelectric element configured to convert ultrasound signals from the ultrasound transducer into electrical signals, a rectifier configured to convert alternating current from the piezoelectric element to a monophasic current, a capacitor coupled to the rectifier, and a first electrode and a second electrode coupled to the rectifier and capacitor and configured to transmit the monophasic current to body tissue. In addition, the apparatus may (Continued)

include a current-limiting circuit configured to limit the amount of current transmitted to the body tissue.

6 Claims, 6 Drawing Sheets

Related U.S. Application Data

(60) Provisional application No. 61/650,082, filed on May 22, 2012.

(56) References Cited

U.S. PATENT DOCUMENTS

| | | | |
|---|---|---|---|
| 5,591,218 A | 1/1997 | Jacobson | |
| 6,324,432 B1 | 11/2001 | Rigaux et al. | |
| 6,924,773 B1 | 8/2005 | Paratte | |
| 7,702,395 B2 | 4/2010 | Towe et al. | |
| 7,894,907 B2 | 2/2011 | Cowan et al. | |
| 7,899,542 B2 | 3/2011 | Cowan et al. | |
| 8,282,561 B2 | 10/2012 | Towe | |
| 8,340,773 B2 | 12/2012 | Towe et al. | |
| 8,369,956 B2 | 2/2013 | Towe et al. | |
| 8,725,270 B2 | 5/2014 | Towe | |
| 8,909,343 B2 | 12/2014 | Towe | |
| 9,446,255 B2 | 9/2016 | Towe et al. | |
| 9,457,196 B2 | 10/2016 | Towe et al. | |
| 9,555,258 B2 | 1/2017 | Towe et al. | |
| 9,693,708 B2 | 7/2017 | Towe | |
| 9,700,712 B2 | 7/2017 | Towe | |
| 10,016,612 B2 | 7/2018 | Towe et al. | |
| 10,022,566 B2 | 7/2018 | Towe | |
| 2006/0167500 A1 | 7/2006 | Towe et al. | |
| 2007/0276232 A1 | 11/2007 | Towe | |
| 2010/0161001 A1 | 6/2010 | Dillbaldi | |
| 2010/0179628 A1 | 7/2010 | Towe et al. | |
| 2011/0077722 A1 | 3/2011 | Towe et al. | |
| 2012/0041310 A1 | 2/2012 | Towe | |
| 2012/0041499 A1 | 2/2012 | Towe et al. | |
| 2013/0096435 A1 | 4/2013 | Towe | |
| 2013/0096656 A1 | 4/2013 | Towe et al. | |
| 2013/0253612 A1 | 9/2013 | Chow | |
| 2015/0148710 A1 | 5/2015 | Towe et al. | |
| 2015/0306429 A1 | 10/2015 | Towe et al. | |
| 2017/0056676 A1 | 3/2017 | Towe et al. | |
| 2017/0095198 A1 | 4/2017 | Towe | |
| 2017/0258363 A1 | 9/2017 | Towe | |
| 2017/0274200 A1 | 9/2017 | Towe | |
| 2018/0093112 A1 | 4/2018 | Towe et al. | |
| 2019/0247668 A1 | 8/2019 | Towe et al. | |

FOREIGN PATENT DOCUMENTS

| | | |
|---|---|---|
| WO | 2008137703 A1 | 11/2008 |
| WO | 2010027963 A1 | 3/2010 |
| WO | 2010135634 A2 | 11/2010 |
| WO | 2011156495 A2 | 12/2011 |
| WO | 2012030962 A2 | 3/2012 |
| WO | 2013071290 A1 | 5/2013 |
| WO | 2013169363 A2 | 11/2013 |
| WO | 2014093332 A1 | 6/2014 |
| WO | 2015069446 A1 | 5/2015 |
| WO | 2015142842 A2 | 9/2015 |

APPARATUS, SYSTEM, AND METHOD FOR NEUROSTIMULATION BY HIGH FREQUENCY ULTRASOUND

CROSS-REFERENCE TO RELATED APPLICATIONS

This application is a continuation of U.S. patent application Ser. No. 14/402,632, filed Nov. 20, 2014, is a national phase application under 35 U.S.C. § 371 of International Application No. PCT/US2013/030812, filed Mar. 13, 2013, which claims the benefit of U.S. Provisional Patent Application No. 61/650,082, filed May 22, 2012, the contents of which applications are hereby incorporated into the present application by reference.

BACKGROUND OF THE INVENTION

Field of the Invention

This invention relates to neurostimulation, and more particularly relates to an apparatus system and method for neurostimulation by high frequency stimulation.

Description of the Related Art

Directly stimulating bioelectrically excitable tissue may be beneficial as a therapeutic tool. For example, neurostimulation may be used for restoring function in cases of neural injury or disease. Neurostimulation as used herein refers to the stimulation of electrically excitable tissues of living things. This can include, for example, the human tissues of the brain, heart, muscle, and nervous system.

Two methods of neurostimulation are the application of pulsed electrical currents directly to tissue through electrodes implanted within tissue and the indirect application of electrical currents through the body surface.

Directly applied electrical currents applied to tissue are known to affect the membranes of excitable cells, causing a depolarizing effect that can lead to a cell action event that depends on its type and biological function. The pulsing of currents is sometimes needed to prevent accommodation to current flows and to fulfill certain physiologic conditions that enables electricity to be effective. Direct application of currents may have the disadvantage of requiring invasive techniques, such as inserting probes or wires into the body.

It is also possible to apply electrical currents to the body surface where they diffuse in the volume conductivity of tissue and attenuate according to well known laws. These currents can also stimulate near-surface nerves and muscle tissues to some degree, but cannot reach deeper tissues because of high electrical losses in tissue and the rise in the needed current levels to above those that would cause electrical shock and tissue damage. It is also difficult to specifically stimulate a particular area of tissue without stimulating surrounding areas.

The strong diffusion of electrical current in tissues from surface electrodes means that specific stimulation of a given nerve or nerve fiber within a bundle is difficult. There is a tendency for electrical currents applied to the body surface to broadly stimulate in undesirable ways. Implantable electrodes overcome these problems but are invasive and suffer from the undesirable need to either run wires through the skin or work with relatively bulky implanted power systems that run on batteries or are powered by external radiofrequency (RF) powering techniques.

SUMMARY OF THE INVENTION

An apparatus for neurostimulation is presented. In one embodiment, the apparatus includes a pulse generator, and an ultrasound transducer coupled to the pulse generator. In some embodiments, the apparatus may include an implantable stimulator. The implantable stimulator may include a piezoelectric element configured to convert ultrasound signals from the ultrasound transducer into electrical signals, a rectifier configured to convert electrical signals from the piezoelectric element (which may be alternating current) to a monophasic current, and a first electrode and a second electrode coupled to the rectifier and configured to transmit the monophasic current to body tissue. In some embodiments, the apparatus may include a current-limiting circuit configured to limit the amount of current transmitted to the body tissue.

In some embodiments, the current-limiting circuit may be coupled to the first electrode and second electrode. In addition, the current-limiting circuit may be a zener diode. In some embodiments, the implantable stimulator further comprises an electrical impedance matching circuit such as a voltage multiplier, charge pump. In some embodiments, the piezoelectric element may comprise a series of elements that are wired in a series or parallel configuration to adjust the output port impedance. In some embodiments, the current-limiting circuit may include a pulse-width modulator configured to modulate a signal from the pulse generator to the ultrasound transducer. In addition, the pulse-width modulator may be configured to produce pulses with on-times between 1 microsecond and 100 microseconds, and may be configured to produce modulated signals that have a duration between 50 microseconds and 500 milliseconds.

In some embodiments, the current-limiting circuit may include a sensor configured to detect reporter signals on or near a skin surface. In addition, the current-limiting circuit may include a power-modification circuit configured to adjust the pulse generator in response to the reporter signals.

In some embodiments, the reporter signals may be electric signals detected by tissue volume conduction from the implant. In some embodiments, the reporter signals may be electromagnetic signals detected by an antenna placed on or in proximity to an implanted device. The reporter signals may be used to determine when the neurostimulator is in saturation.

A method for providing neurostimulation is also provided. In some embodiments, the method may include emitting a first electrical signal from a pulse generator. In addition, in some embodiments, the method may include emitting an ultrasound signal from an ultrasound transducer coupled to the pulse generator. In some embodiments, the method may include receiving the ultrasound signal in an implantable stimulator. In some embodiments, the method may include converting the received ultrasound signal to an electrical current. In addition, the method may include limiting the current in a current-limiting circuit configured to limit the amount of current transmitted to the body tissue. In some embodiments, the method may include conducting (flowing) the electrical current to body tissue through the first electrode and second electrode.

In some embodiments, the method may include detecting reporter signals produced by the implantable stimulator on or near a skin surface. In addition, the method may include modulating the pulse generator in response to the reporter signals to adjust the amount of current flowed through the body tissue. In some embodiments, detecting the reporter signals may be performed with a loop antenna. In some embodiments, detecting the reporter signals may be performed with surface electrodes on the skin.

In some embodiments, the method may include determining a change in stimulation current by detecting a change in the amplitude of the reporter signals. Furthermore, due to the acoustic transit time of an emitted ultrasound pulse detecting the reporter signal may be performed after an end of the emitted ultrasound signal.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, the method may include detecting reporter signals only during a calibration phase. However, in some embodiments, the method may include constantly detecting reporter signals to adjust the output of the implantable neurostimulator. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
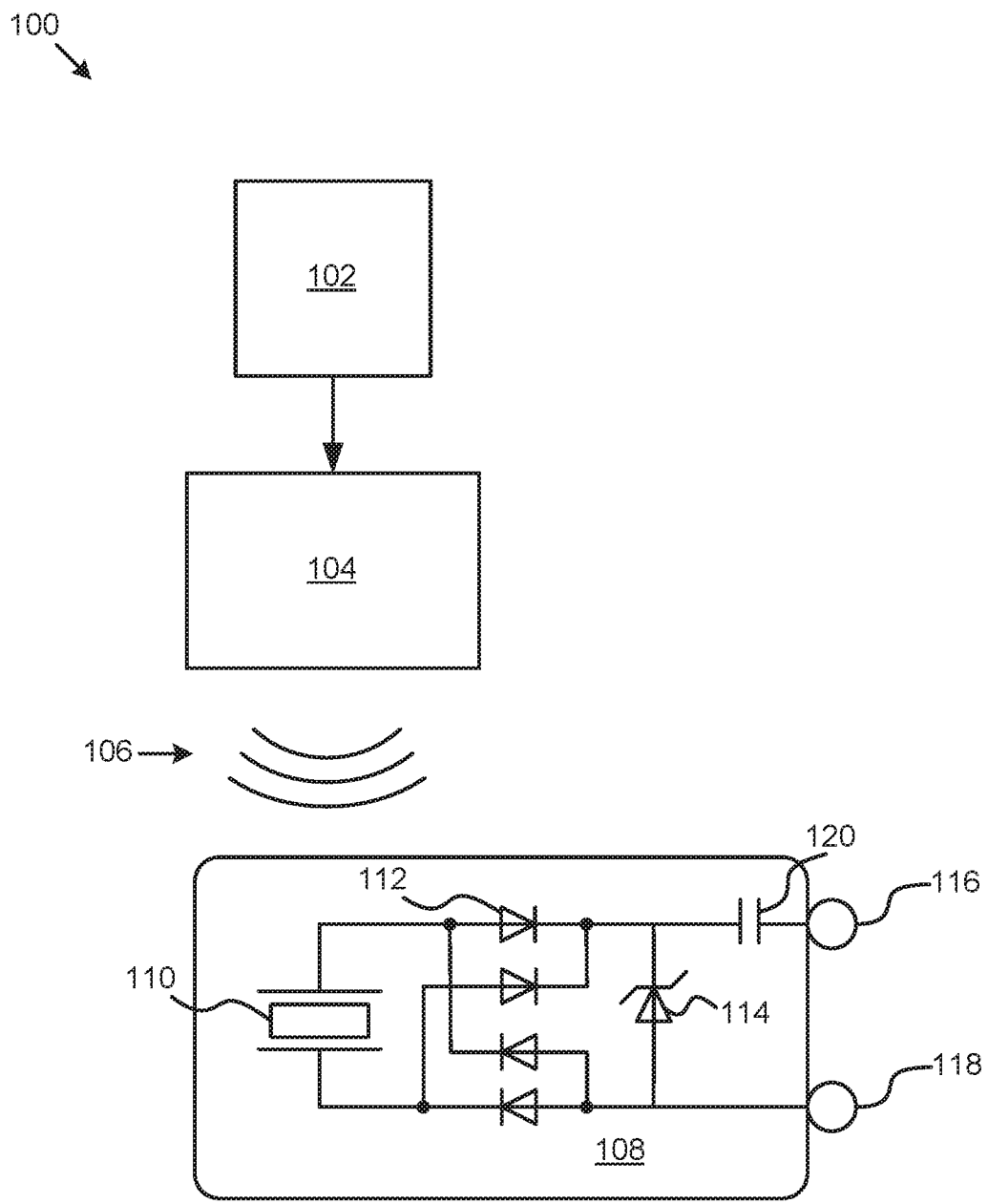
FIG. 1 is a schematic block diagram illustrating one embodiment of an implantable neurostimulator.

FIG. 1 illustrates one embodiment of a system 100 for neurostimulation by high frequency ultrasound. In one embodiment, the system 100 includes a pulse generator 102. Coupled to the pulse generator 102 is an ultrasound transducer 104 that can convert electrical signals created by the pulse generator 102 into ultrasound signals 106. The ultrasound signals can vary in shape, duration, and length. For example, electrical signals from the pulse generator 102, and the corresponding ultrasound signals 106, may be a train of pulses of a fixed or variable frequency, duty-cycle, and duration.

System 100 also includes an implantable stimulator 108. The implantable stimulator includes a piezoelectric element 110 that is configured to convert ultrasound signals 106 from the ultrasound transducer 104 into electrical signals. The implantable stimulator 108 also includes a rectifier 112 configured to convert alternating current from the piezoelectric element 110, which is an alternating current, into a monophasic current. The rectifier may be a half-wave, or a full-wave rectifier. For example, as shown in FIG. 1, four diodes 112 create a full-wave rectifier that converts the output of the piezoelectric element 110 into a monophasic current.

System 100 includes a first electrode 116 and a second electrode 118 coupled to the rectifier 112 and configured to transmit the monophasic current to body tissue. The body tissue may be any body tissue in humans or animals. For example, the body tissue into which the monophasic current is transmitted by the electrodes 116, and 118 may be part of the central or peripheral nervous system, or tissue associated with those nervous systems. System 100 also includes a current-limiting circuit configured to limit the amount of current transmitted to the body tissue. In this embodiment, the zener diode 114 is configured to limit the maximum voltage that can be transmitted to the electrodes, and therefore limit the current transmitted to the body tissue. Other components that may limit the voltage transmitted to the electrodes include a PIN diode, a metal oxide varistor, avalanche conduction diodes, as well as a system of components that may have an abrupt current conduction above a particular threshold voltage. The zener diode 114 is coupled to the first electrode 116 by capacitor 120. In some embodiments, the capacitor may have a capacitance of about 1-10 µF. In some embodiments, the capacitor 120 may be replaced by a charge balancing circuit.

In some embodiments, the implantable stimulator 108 may include a voltage multiplier to increase the voltage delivered to the body tissue. The voltage multiplier may help match the impedance of the body tissue to control the amount of neurostimulation. For example, the voltage multiplier may be a Cockroft-Walton multiplier that uses a series of diodes and capacitors to convert an AC voltage into a higher DC voltage. In addition, the voltage multiplier may include charge pumps or buck-boost circuits, for example. In some embodiments, the output circuit is directly coupled to electrodes such that monophasic currents flow in tissue. This may be desirable in certain electrical stimulation applications such as where currents are applied to bone to promote improved osteogenesis. The high frequency monophasic current is smoothed to an average level by the capacitive nature of cell membranes and has been found effective in stimulating tissue. At the electrode-tissue interface there is a complex combination of resistive and capacitive natures as well as a charge storage capability which responds to the monophasic current by acquiring the envelop of the monophasic pulse train. This presents a relatively lower frequency stimulation pulse to the tissue that then responds as would a electrical pulse having the duration of the envelope of the pulse. This lower frequency monophasic pulse however needs to be compensated by a reverse low frequency current flow in applications where net currents through electrodes produce undesired tissue reactions. Capacitive coupling of low frequency currents by an output coupling capacitor helps in the charge recovery. Electrical current flows through the tissue so as to inhibit the build up of undesirable products of electrochemistry that emit from electrodes when currents are passed through them in body tissue. This capacitor may be replaced by other methods of stimulating electrode charge balancing such as active circuits.

The current-limiting circuit may also include a pulse-width modulator configured to modulate a signal from the pulse generator to the ultrasound transducer. For example, electrical signals produced by the pulse generator 102 may be a train of pulses that vary in frequency, duty-cycle and/or duration. For example, the pulse generator 102 may be configured to produce pulses with on-times of 1 to 100 microseconds. The ultrasound transducer 104 may then convert those signals to ultrasound signals 106. In addition, pulse generator may be configured to produce pulse-width modulated signals that have a duration of 50 microseconds to 500 milliseconds. In addition, the frequency of the pulse width modulated signal can be varied. For example, if a signal has an on time of 1 microsecond, a duty-cycle of 50%, and a duration of 1 millisecond, the output signal will include 500 pulses.

Figure 2:
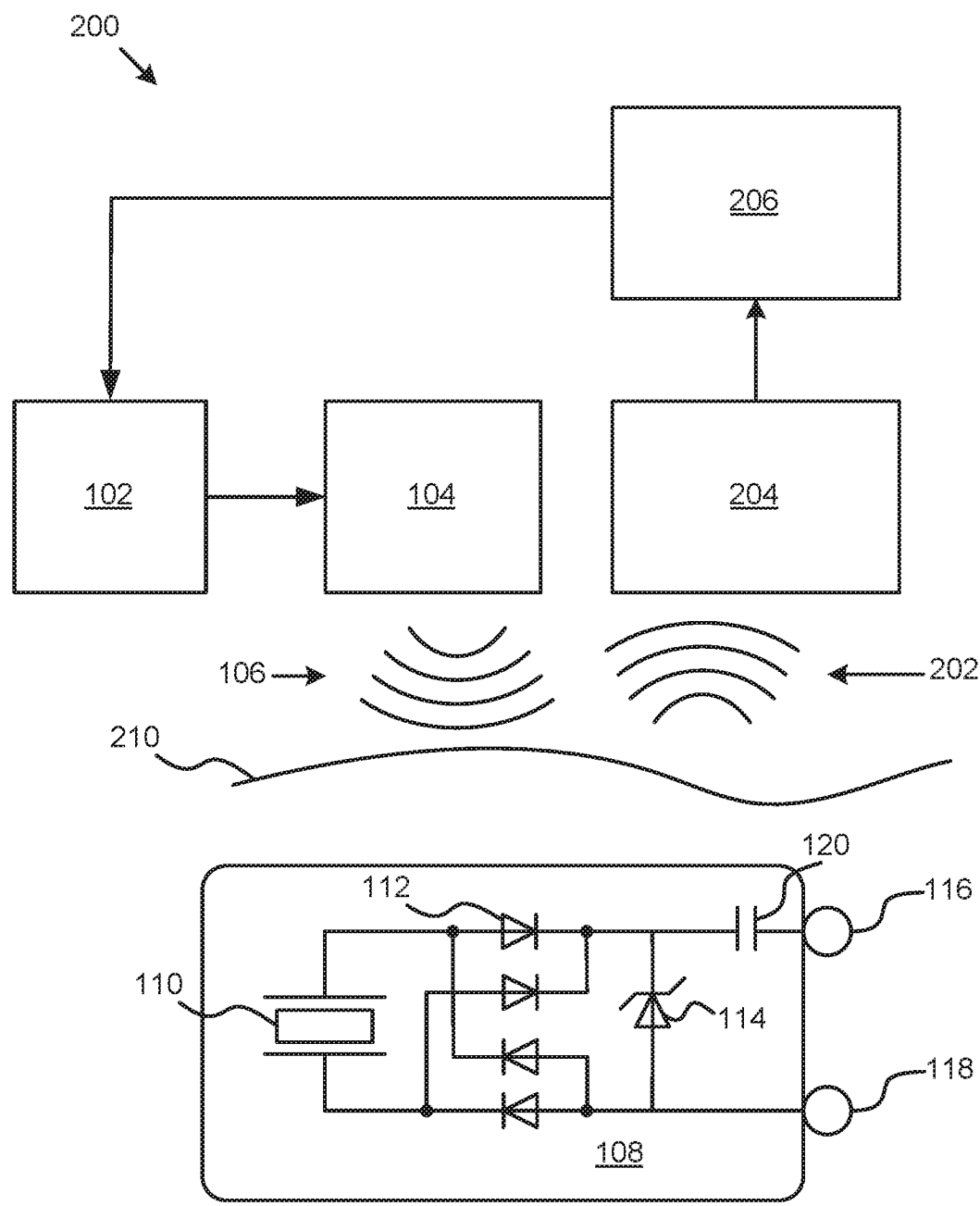
FIG. 2 is a schematic block diagram of one embodiment of an implantable neurostimulator with feedback control.

FIG. 2 illustrates a system 200 for neurostimulation. System 200 includes the pulse generator 102, the ultrasound transducer 104, the ultrasound signal 106, the piezoelectric element 110, the rectifier 112, the zener 114, capacitor 120, and electrodes 116 and 118 as described in connection with FIG. 1. In addition, system 200 includes a sensor 204 configured to detect signals 202 on or near a skin surface 210. The signals may be electrical signals or electromagnetic signals that can be detected at the skin surface 210. The sensor 204 may be an electrode coupled to the skin surface where the electrode is configured to detect electric signals that travel through body tissue. In some embodiments, the sensor 204 may be configured to detect electromagnetic signals, or radio-frequency signals. For example, a loop antenna may be configured to detect radiofrequency signals near the skin surface 210.

System 200 also includes a power-modification circuit 206 configured to adjust the pulse generator 102 in response to the detected signals 202. The feedback from the sensor 204 can be used to limit or increase the amount of current that is delivered to the body tissue.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 3:
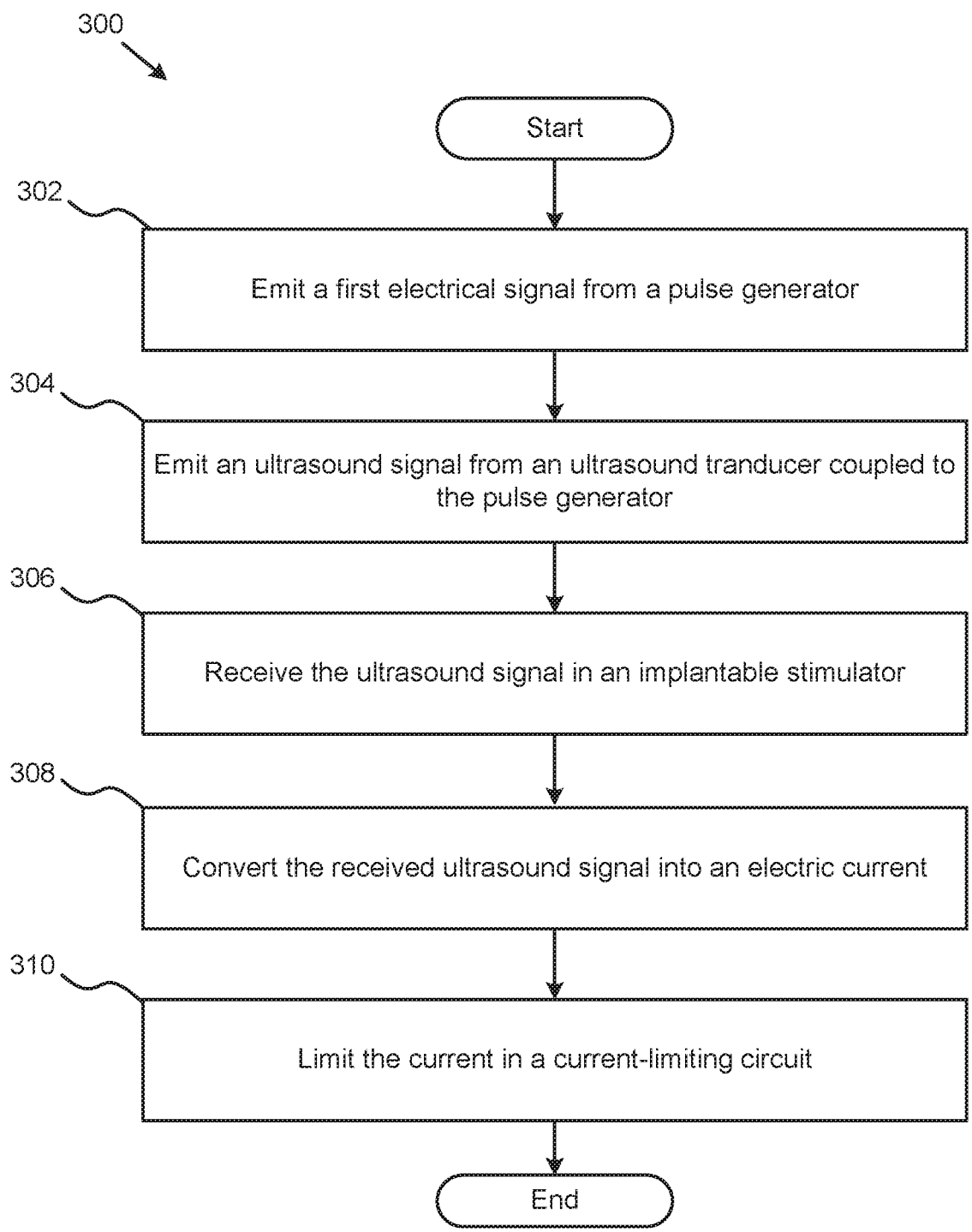
FIG. 3 is a flow chart diagram depicting one embodiment of a method for providing neurostimulation.

FIG. 3 illustrates a schematic flow diagram of a method for providing neurostimulation. In this embodiment, the method 300 begins by emitting 302 a first electrical signal from a pulse generator. As described above in connection with FIGS. 1 and 2, the signal from the pulse generator may be modulated to vary in frequency, duty-cycle, and duration. The method also includes emitting 304 an ultrasound signal from an ultrasound transducer coupled to the pulse generator. The ultrasound transducer 304 may be, for example, a piezoelectric ultrasound transducer.

Method 300 also includes the step of receiving 306 the ultrasound signal in an implantable stimulator, such as the implantable stimulator described in connection with FIG. 1 above. In step 308, the method converts 308 the received ultrasound signal to an electrical current in the implantable stimulator. In addition, the method includes the step of limiting 310 the current in a current-limiting circuit. By limiting the current, the amount of electrical stimulation delivered to the body can be controlled. Limiting the current can create reproducible and safe neurostimulation while reducing unwanted effects of neurostimulation, such as providing too much current.

The step of limiting 310 the current in a current-limiting circuit may include further steps for detecting how much current is produced by the implantable neurostimulator. In some embodiments, a reporter signal may be measured, where the reporter signal can be an electric signal, a radio frequency signal, or an acoustic signal emitted by the implantable neurostimulator. The acoustic signal is emitted by the neurostimulator piezoelectric elements as they resonate and have a prolonged ring-down after being excited by the pulse generator. The amplitude of the acoustic response, since it is directly coupled to the limiting circuit, is modulated in the same way as the amplitude of electric signal.

In one embodiment, a reporter signal, a radiated radiofrequency emission of the implanted neurostimulator 108, is used as an indication of the amount of current created by the neurostimulator. The radiofrequency signal can be measured by a loop antenna. The sensor 104 is tuned to the second harmonic of the neurostimulator ultrasound signal 106 frequency. The harmonic emission from the neurostimulator may be distorted compared to the ultrasound signal 106. For example, the distortion may be caused by the nonlinear behavior of the neurostimulator components, such as the rectifier 112 or the zener diode 114. Although the second harmonic may be stronger than other harmonics, and therefore be better suited for detection, other harmonics may also be used to detect the amount of current delivered to the body tissue by the implanted neurostimulator. The amplitude of the response measured by the sensor 204 may indicate that the implanted neurostimulator is in saturation. For example, when the voltage created by the piezoelectric element 110 and rectifier 112 rises above the breakdown voltage of zener diode 114, the neurostimulator is operating in saturation. By ramping up the output of the pulse generator and measuring the point when the amplitude of the response reduces its rate of increase, the system can determine the intensity of the pulse generator's output required to place the implantable neurostimulator in saturation. That power can then be used for deliver a known amount of voltage for neurostimulation. In some embodiments, the amplitude of the pulse generator can be increased by a predetermined amount (e.g. 20%) over what is necessary to place the neurostimulator in saturation to ensure that the neurostimulator reaches saturation with subsequent pulses. In some embodiments, the amplitude of the pulse generator can be decreased by a predetermined amount. The number of subsequent pulses can then be used to vary the amount of stimulation delivered by the neurostimulator.

In some embodiments, the reporter signal may be an electric signal emitted through the electrodes of the implantable neurostimulator. The electric signals may be detected using skin electrodes and used to determine when the neurostimulator is in saturation.

In some embodiments, the acoustic transit time it takes an ultrasound signal to reach the neurostimulator can be used to separate the electrical artifact signal generated by the pulse generator from the received radio frequency, such as the second harmonic. By separating the pulse generated by the pulse generator and the received radiofrequency signal, noise from the pulse generator can be removed from the detected radiofrequency signal. As such, the received signal can be measured with greater accuracy to determine when the neurostimulator is in saturation. In some embodiments, the ultrasound transducer may be configured to suppress harmonic artifact emissions to allow more accurate readings of the received radio frequency.

In some configurations with suitably short ultrasound pulses on the order of 0.5 to 5 microseconds, the acoustic transit time delay of the emitted pulse can be used advantageously to separate the electrical artifact emitting from the ultrasound transducer from the detected response monitored from body surface electrodes or an loop antenna. In this configuration the entire electrical evoked response from the neurostimulator regardless of its frequency components may be detected and used for purposes of feedback controlling the power or determining the status if the implant. For example, the response may be used to determine whether the stimulator is functional. This method is advantageous in that such short ultrasound pulses are insufficient to evoke neurostimulation and so allow for a method of assessing neurostimulator currents that will flow with longer signal duration on the order of 25 microseconds to 50 milliseconds without causing stimulation of the tissue. This allows for interrogation pulses to assess the neurostimulation current flow prior to emitting longer signals that will then appreciably stimulate tissue.

Figure 4:
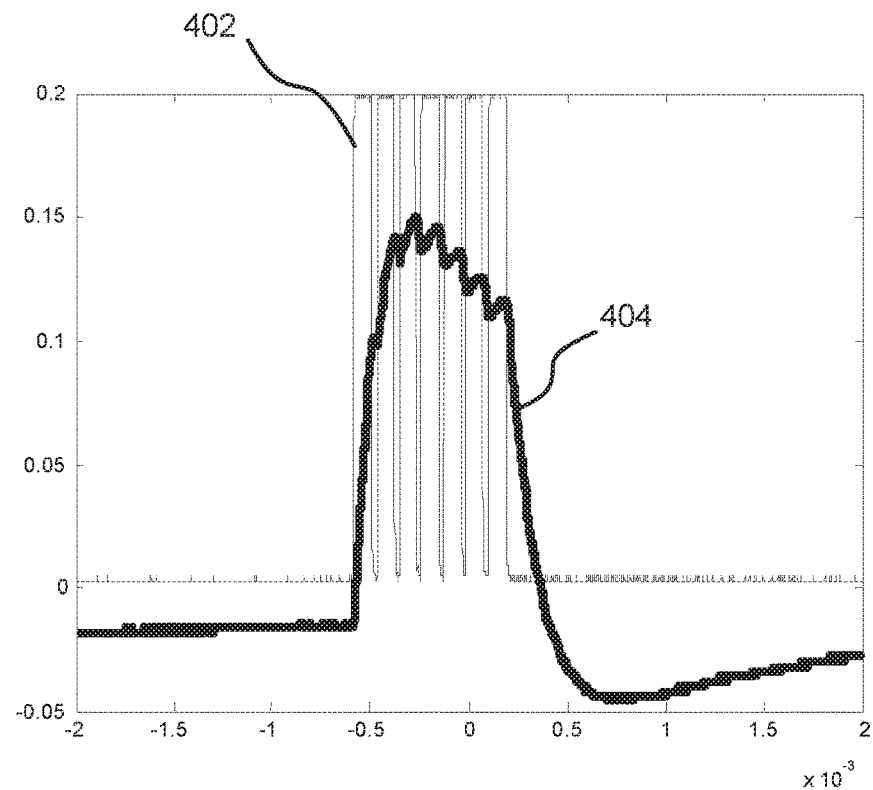
FIGS. 4-6 are graphical representations of neurostimulation simulations with pulse width modulated signals.
Figure 5:
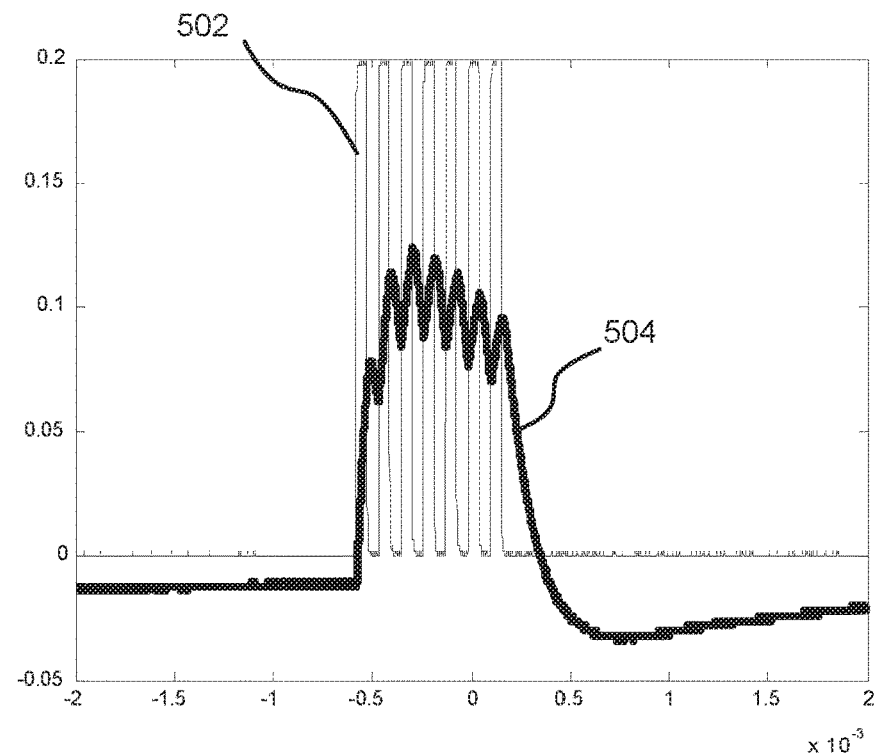
Figure 6:
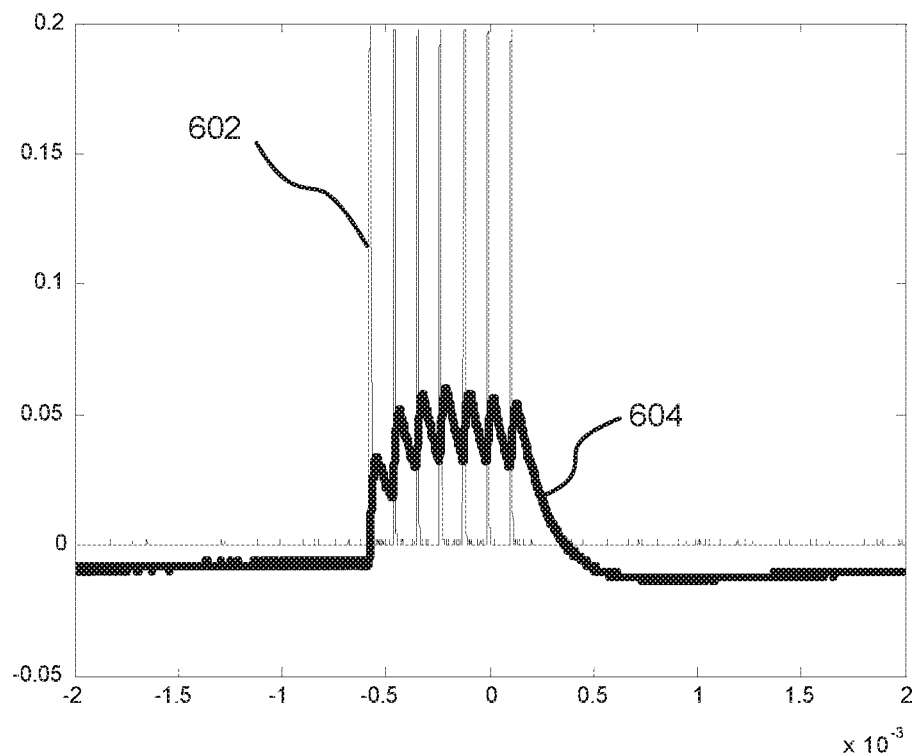

FIGS. 4-6 show results of simulations of neurostimulation provided by an implantable neurostimulator, such as that described above in connection with FIGS. 1 and 2. The signal 402 represents the output of the pulse generator 102 having a duty-cycle of about 90%. The signal 404 represents the amount of current provided by the implantable stimulator to simulated body tissue. As shown in FIG. 4, the stimulation current 402 causes a pulse 404. Although signal 404 does show some ripples caused by the individual pulses of signal 402, the simulated body tissue acts as a low-pass filter and results in a pulse of longer duration that may be more useful for neurostimulation.

FIG. 5 shows the same simulation as shown in FIG. 4, but the pulses in signal 502 have a lower duty cycle, around 50%, than the pulses in signal 402. The resulting output current 504 shows a reduced amplitude as compared to current 404. By modifying the duty-cycle of the stimulating signals 402 and 502, the amplitude of the signals 404 and 504 delivered to the simulated body tissue can be controlled. FIG. 6 shows the results of a similar simulation, where the stimulating signal 602 has a duty-cycle of about 10% and causes the output current 604 to be reduced in amplitude compared to output currents 404 and 504.

Figure 7:
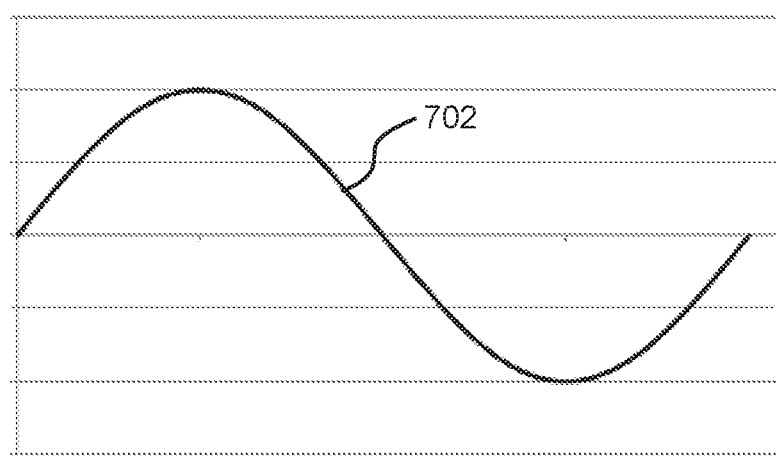
FIGS. 7-8 are graphical representations of neurostimulation signals.
Figure 8:
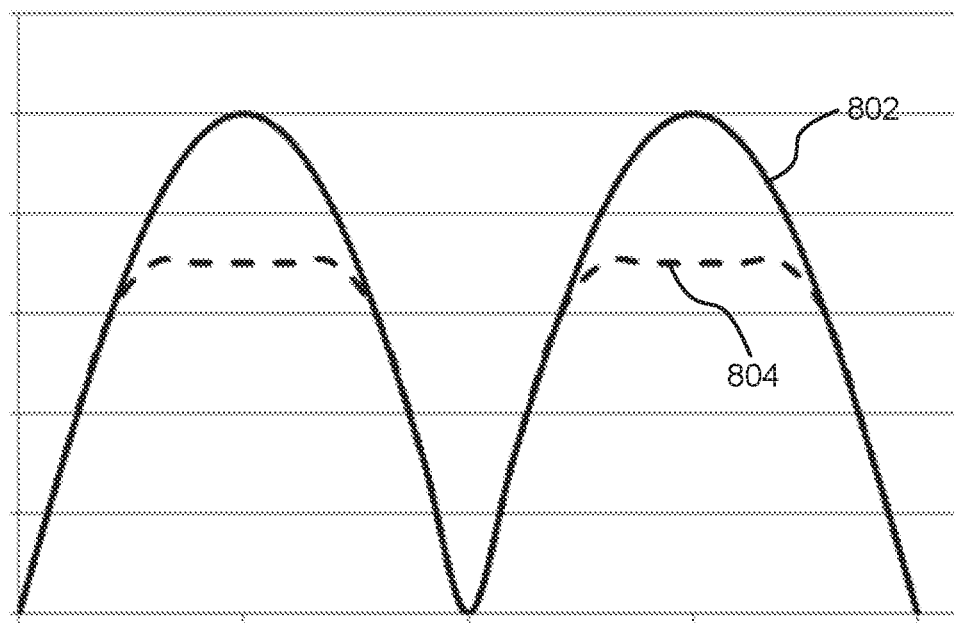

FIGS. 7 and 8 show an example of how the zener diode 114 in FIG. 1 can limit the output voltage, and as a result, the output current of the implantable neurostimulator. Signal 702 in FIG. 7 represents the output of the pulse generator 102. Signal 802 shows the output of the full-wave rectifier created by diodes 112. Finally, output signal 804 shows the effect of the zener diode 114. When the signal 802 rises above the breakdown voltage of zener diode 114, the implantable neurostimulator output signal is limited to that voltage. As such, the output voltage, and concomitant current used for neurostimulation is limited.

Figure 9:
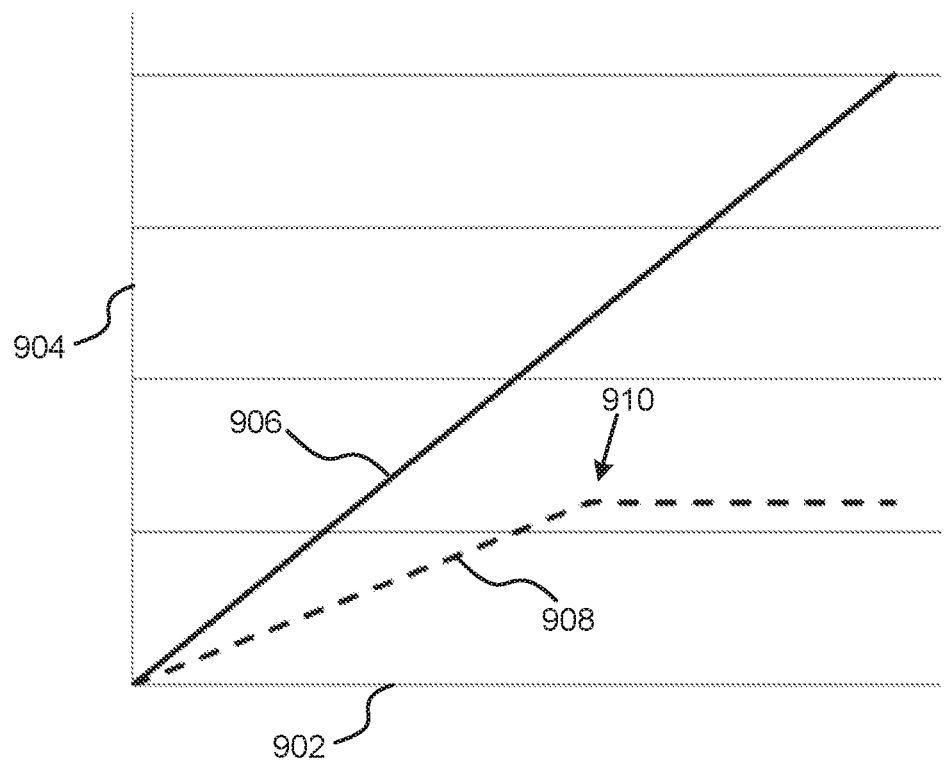
FIG. 9 shows one embodiment of the relationship between the output of a pulse generator and a reporter signal from a neurostimulator.

FIG. 9 shows an example of the relationship between the output of the pulse generator and the reporter signal emitted by the neurostimulator. In this example, the x-axis 902 represents time, and the y-axis represents amplitude. Signal 906 represents the output of the pulse generator—the output increases over time. As the pulse generator output, and the corresponding ultrasound output increase, the current delivered to the body tissue also increases. As the current delivered to the body tissue increases, the reporter signal 908 also increases. However, when the neurostimulator reaches saturation, the amount of current delivered to the body tissue will plateau at 910. The output of the pulse generator may continue to increase, but the reporter signal does not.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

The invention claimed is:

1. A neurostimulation system with feedback control comprising:
   a variable electrical signal pulse-generator;
   an ultrasound transducer coupled to the variable electrical signal pulse-generator;
   a subcutaneous implant;
   a sensor configured to detect subcutaneous electromagnetic signals from the subcutaneous implant; and
   a power modification circuit configured to adjust signals being generated by the variable electrical signal pulse-generator in response to the subcutaneous electromagnetic signals detected by the sensor,
   wherein the subcutaneous implant is not physically connected to the sensor and is not physically connected to the variable electrical signal pulse-generator;

wherein the subcutaneous implant comprises:
   a piezoelectric element configured to convert ultrasound signals from the ultrasound transducer into alternating current,
   a rectifier configured to convert the alternating current from the piezoelectric element to a monophasic current,
   a capacitor coupled to the rectifier,
   an electrode coupled to the rectifier and to the capacitor, the electrode configured to transmit the monophasic current to body tissue, and
   a current-limiting circuit coupled to the electrode and configured to limit an amount of the monophasic current transmitted to the body tissue via the electrode;
wherein the signal adjustment of the power modification circuit includes modulating the variable electrical signal pulse-generator in response to the detected electromagnetic signals to adjust the amount of current flowed through body tissue from the subcutaneous implant;
wherein the sensor is configured to measure an amplitude of the detected electromagnetic signals and is used to determine if the subcutaneous implant is operating in a saturation state; and
wherein the power modification circuit is configured to measure a point where the amplitude of the detected electromagnetic signal reduces its rate of increase and then to determine an intensity of output of the variable electrical signal pulse-generator required to place the subcutaneous implant in saturation.

2. The neurostimulation system of claim 1 wherein the sensor comprises a loop antenna.

3. The neurostimulation system of claim 1 wherein the pulse generator is configured to generate a train of fixed frequency pulses and a train of variable frequency pulses.

4. The neurostimulation system of claim 1 wherein the pulse generator is configured to generate a train of fixed duty-cycle pulses and a train of variable duty cycle pulses.

5. The neurostimulation system of claim 1 wherein the pulse generator is configured to generate a train of fixed duration pulses and a train of variable duration pulses.

6. The neurostimulation system of claim 1 wherein the implant is biocompatible, and
   wherein the current-limiting circuit comprises a voltage limiting Zener diode.

* * * * *